United States Patent [19]
Ramzipoor et al.

[11] Patent Number: 5,807,355
[45] Date of Patent: Sep. 15, 1998

[54] CATHETER WITH RAPID EXCHANGE AND OTW OPERATIVE MODES

[75] Inventors: Kamal Ramzipoor, Union City; Troy L. Thornton, San Francisco, both of Calif.

[73] Assignee: Advanced Cardiovascular Systems, Inc., Santa Clara, Calif.

[21] Appl. No.: 762,297

[22] Filed: Dec. 9, 1996

[51] Int. Cl.⁶ .................................................. A61M 25/00
[52] U.S. Cl. .......................... 604/282; 604/280; 604/96; 606/192; 606/194
[58] Field of Search .......................... 604/282, 96, 264, 604/280; 606/192, 194

[56] References Cited

U.S. PATENT DOCUMENTS

| | | | |
|---|---|---|---|
| Re. 34,633 | 6/1994 | Sos et al. | 128/772 |
| 4,616,652 | 10/1986 | Simpson | 128/344 |
| 4,917,666 | 4/1990 | Solar et al. | 604/95 |
| 5,135,535 | 8/1992 | Kramer | 606/194 |
| 5,146,925 | 9/1992 | Snow | 128/658 |
| 5,170,787 | 12/1992 | Lindegren | 128/642 |
| 5,328,472 | 7/1994 | Steinke et al. | 604/102 |
| 5,395,334 | 3/1995 | Keith et al. | 604/102 |
| 5,466,222 | 11/1995 | Ressemann et al. | 604/96 |
| 5,484,409 | 1/1996 | Atkinson et al. | 604/96 |
| 5,569,200 | 10/1996 | Umeno et al. | 604/96 |
| 5,599,326 | 2/1997 | Carter | 604/282 |
| 5,649,909 | 7/1997 | Cornelius | 604/96 |

*Primary Examiner*—Corrine M. McDermott
*Assistant Examiner*—Cris L. Rodriguez
*Attorney, Agent, or Firm*—Heller Ehrman White & McAuliffe

[57] ABSTRACT

An intravascular catheter having a relatively long proximal shaft portion, a relatively short distal shaft section and a flexible intermediate shaft which allows the articulation of the distal and proximal shaft sections. The intermediate shaft section has a guidewire port in fluid communication with a guidewire receiving inner lumen which extends through the catheter shaft. In one presently preferred embodiment the portion of the intermediate shaft section through which the guidewire lumen extends is formed by a helical coil having an expanded portion which defines the guidewire port. The catheter allows both rapid exchange and over-the-wire modes of operation.

6 Claims, 3 Drawing Sheets

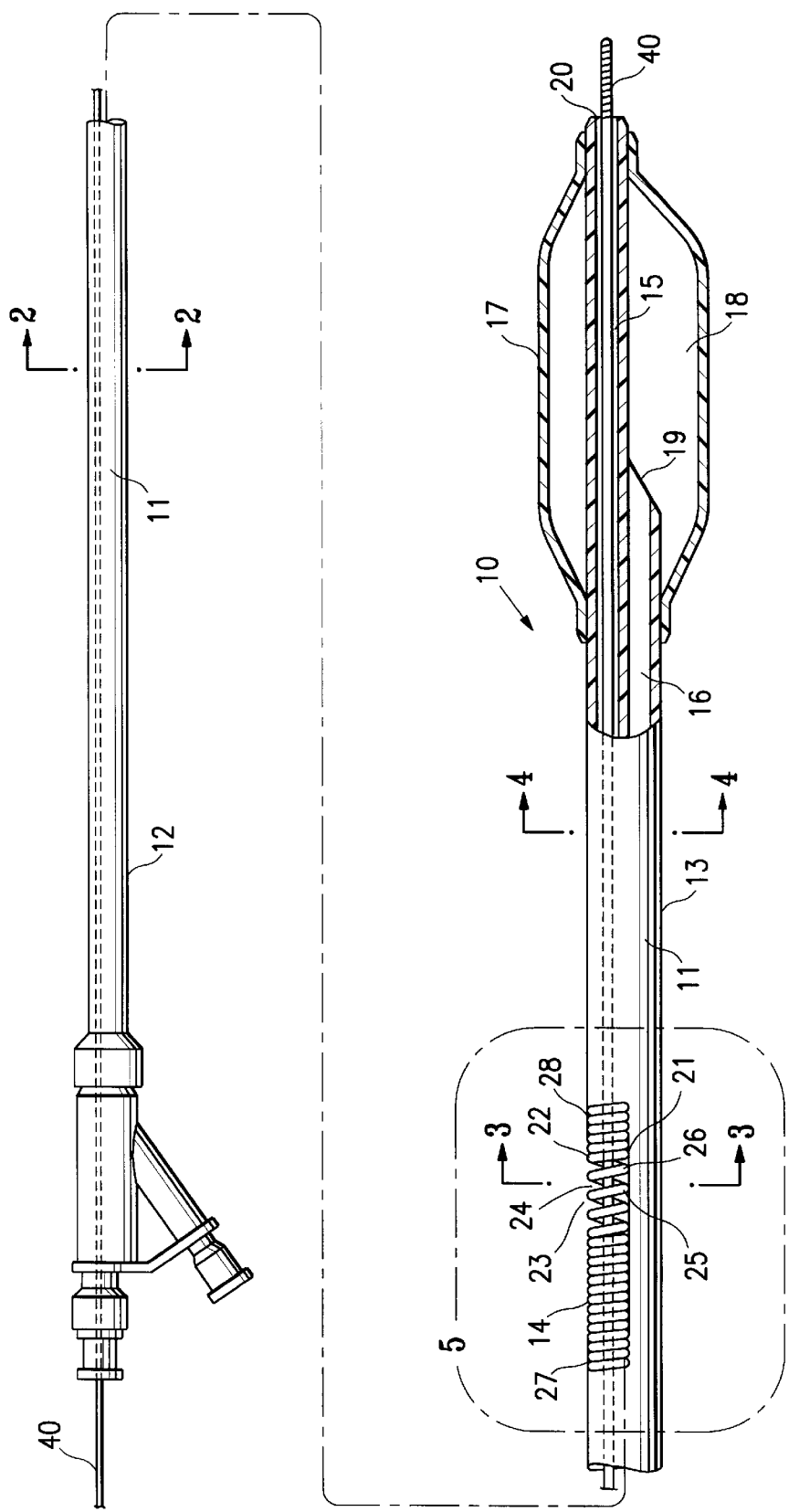

CATHETER WITH RAPID EXCHANGE AND OTW OPERATIVE MODES

BACKGROUND OF THE INVENTION

This invention generally relates to intravascular procedures, such as percutaneous transluminal coronary angioplasty (PTCA), and particularly to an intravascular catheter which can be utilized in a rapid exchange or over-the-wire (OTW) operating mode).

In typical PTCA procedures, a dilatation catheter is advanced over a guidewire slidably disposed within an inner lumen of the dilatation catheter into the patient's coronary artery until the balloon on the distal extremity of the dilatation catheter is properly positioned across the lesion to be dilated. Once properly positioned across the lesion, the flexible, relatively inelastic dilatation balloon on the catheter is inflated to a predetermined size with radiopaque liquid at relatively high pressures (e.g., generally 4–20 atmospheres or more) to dilate the stenosed region of the diseased artery. One or more inflations of the balloon may be required to complete the dilatation of the stenosis. After the last dilatation, the balloon is deflated so that the dilatation catheter can be removed from the dilated stenosis and so that blood flow can resume through the dilated artery.

One significant improvement in dilatation catheters has been the introduction of rapid exchange type dilatation catheters. These catheters have a short guidewire receiving sleeve or inner lumen extending through the distal portion of the catheter which extend from a distal guidewire port in the distal end of the catheter to a proximal guidewire port spaced proximal to the proximal end of the dilatation balloon. The proximal guidewire port is usually located at least about 10 cm and usually not more than about 50 cm from the distal guidewire port. A slit is preferably provided in the catheter wall which extends from the second guidewire port, preferably to a location proximal to the proximal end of the inflatable balloon to aid in the removal of the catheter from a guidewire upon withdrawal of the catheter from the patient. The structure of the catheter allows for the rapid exchange of the catheter without the need for the use of an exchange wire or adding a guidewire extension to the proximal end of the guidewire. The design of this catheter has been widely praised by the medical profession and has met with much commercial success in the market place because of its unique design. The rapid exchange type dilatation catheters of the assignee of the present invention, Advanced Cardiovascular Systems, Inc., have had a significant impact in the market for rapid exchange type dilatation catheters. Such products include dilatation catheters sold under the trademark the ALPHA, the STREAK and the ELLIPSE.

Rapid exchange type dilatation catheters are described and claimed in U.S. Pat. No. 5,040,548 (Yock), U.S. Pat. No. 5,061,273 (Yock), U.S. Pat. No. 5,300,085 (Yock), U.S. Pat. No. 5,350,395 (Yock) and U.S. Pat. No. 4,748,982 (Horzewski et al.), U.S. Pat. No. 5,154,725 (Leopold) and U.S. Pat. No. 5,346,505 (Leopold) which are incorporated herein in their entirety by reference.

However, there is one significant inconvenience with the use of rapid exchange type dilatation catheter systems, namely, the inability to remove a guidewire already in place within a patient's vasculature during an angioplasty procedure without losing access to the vascular location. There has been no convenient way in which to withdraw an in-place guidewire and then advance a replacement guidewire without losing access to the location of the distal end of the rapid exchange type dilatation catheter the short guidewire receiving inner lumen in the distal extremity of a rapid exchange type dilatation catheter. These instances occur when there is a need to replace an in-place guidewire with another guidewire having a different structure, e.g. from a floppy-type design with a separate shaping ribbon to an intermediate or standard with a core wire which extends to the distal tip of the guidewire. The need to withdraw an in-place guidewire also occurs when the distal tip of the in-place guidewire needs to be reshaped.

U.S. Pat. No. 5,135,535 (Kramer), which has been assigned to the present assignee, Advanced Cardiovascular Systems, Inc., describes an intravascular catheter which may be used in both a rapid exchange and over-the-wire mode and thereby allows an in-place guidewire to be replaced. The Kramer patent is incorporated herein by reference. While this catheter had significant advantages over other intravascular catheters, mounting an in-place guidewire was found to be difficult because of the difficulty in advancing the proximal end of a guidewire out the proximal guidewire port. The present invention satisfies these and other needs.

SUMMARY OF THE INVENTION

This invention is directed to an elongated intravascular catheter which can be utilized in a rapid exchange or an over-the-wire mode of operation to perform an intravascular procedure, and particularly to a balloon dilatation catheter which can be used within the coronary arteries of a human patient during an angioplasty procedure.

The intravascular catheter of the invention generally comprises an elongated shaft with proximal and distal ends, a port in the distal end, a first lumen extending therein from the proximal end to an opening in the distal end of the catheter and a second lumen extending therein to a location spaced proximally from the distal end. The catheter shaft has an elongated proximal section, a relatively short distal section and a balloon or other means to perform an intravascular procedure on the distal section which is in communication with the second lumen. An intermediate section is provided between the proximal and distal sections which has a longitudinally expandable wall defining at least in part a portion of the first lumen extending therethrough. The intermediate section should also be capable of transmitting push from the proximal shaft section to the distal shaft section and should be sufficiently longitudinally flexible to allow the articulation of the distal shaft section with respect to the proximal shaft section. An opening is provided in the longitudinally expandable wall of the intermediate section which is in fluid communication with the portion of the first lumen extending therethrough. This structure allows the proximal end of a guidewire to be back loaded through the first opening in the distal end of the shaft and the first lumen extending within the distal section and with the distal section articulated with respect to the proximal section, out the opening provided in the longitudinally expandable intermediate section. The intravascular catheter can be advanced over an in-place guidewire while holding onto the proximal extremity of the guidewire extending out of the patient, until the distal end of the catheter is disposed within a desired location of the patient's vascular system. The in-place guidewire is external of the catheter proximal to the opening in the intermediate shaft section of the catheter. In this manner, the in-place guidewire can be removed by pulling on the proximal extremity thereof which extends out the patient and a replacement guidewire can be introduced into the proximal end of the catheter shaft, advanced through catheter shaft in the first lumen thereof and then out the opening in the distal end of the catheter.

For coronary artery use, the second opening in the intermediate shaft section is preferably spaced longitudinally at least 10 cm from the distal end of the catheter shaft to ensure that it remains within a guiding catheter when the distal shaft section extends out into the patient's coronary artery.

In one embodiment, the intermediate shaft section is formed in part of a helical coil with the second opening therein being defined at least in part by two adjacent turns of an expanded part of the helical coil.

One presently preferred embodiment of the invention is in the form of a balloon dilatation catheter for performing an angioplasty procedure within the coronary arteries of a human patient. In this presently preferred embodiment, the first lumen of the catheter shaft is a guidewire receiving lumen and the second lumen is a inflation lumen adapted to direct inflation fluid to the interior of a dilatation balloon on the distal shaft section.

To mount the catheter of the invention onto a guidewire, the either the proximal shaft section or the distal shaft section is manually or otherwise articulated with respect to the other catheter shaft section so as to bend the intermediate shaft section and to thereby align the second guidewire opening with the first guidewire lumen. In this manner, the proximal end of guidewire can be introduced into the first guidewire lumen through the first opening in the distal end of the catheter and advanced proximally through the first guidewire lumen until the proximal end of the guidewire passes out the second guidewire opening. Usually, while the intermediate shaft section longitudinally flexible to facilitate the articulation, it has enough resiliency to return to an essentially straight shape when the force applied to the catheter shaft to effect the articulation is released. The catheter may then be advanced over the guidewire to a desired location within a patient's vasculature as described in the Background of the Invention. If it is necessary to remove the in-place guidewire during the procedure, the in-place guidewire can be easily removed by pulling on the proximal extremity thereof which extends out of the patient. A replacement guidewire can then be advanced through the portion of the first guidewire receiving lumen in the proximal shaft section into and through the portion of the first guidewire receiving lumen in the intermediate and the distal shaft sections. These and other advantages of the invention will become apparent from the following detailed description of the invention when take in conjunction with the accompanying exemplary drawings.

BRIEF DESCRIPTION OF THE DRAWINGS

FIG. 1 is an elevational view, partially in section, of a presently preferred embodiment of the invention.

DETAILED DESCRIPTION OF THE INVENTION

Figure 4:
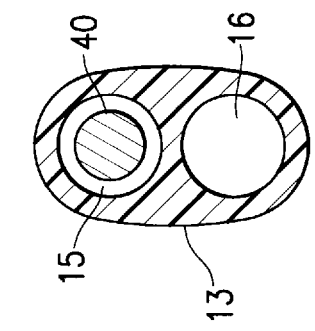
FIG. 4 is a transverse cross-sectional view of the embodiment shown in FIG. 1 taken along the lines 3—3
Figure 3:
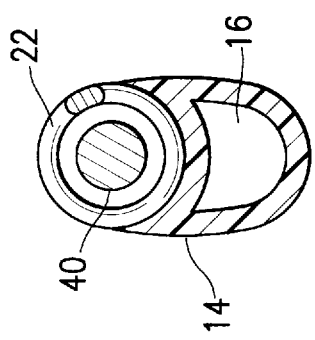
FIG. 3 is a transverse cross-sectional view of the embodiment shown in FIG. 1 taken along the lines 3—3.
Figure 2:
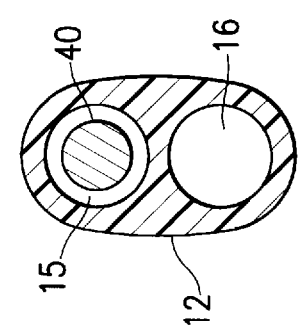
FIG. 2 is a transverse cross-sectional view of the embodiment shown in FIG. 1 taken along the lines 2—2.
Figure 5:
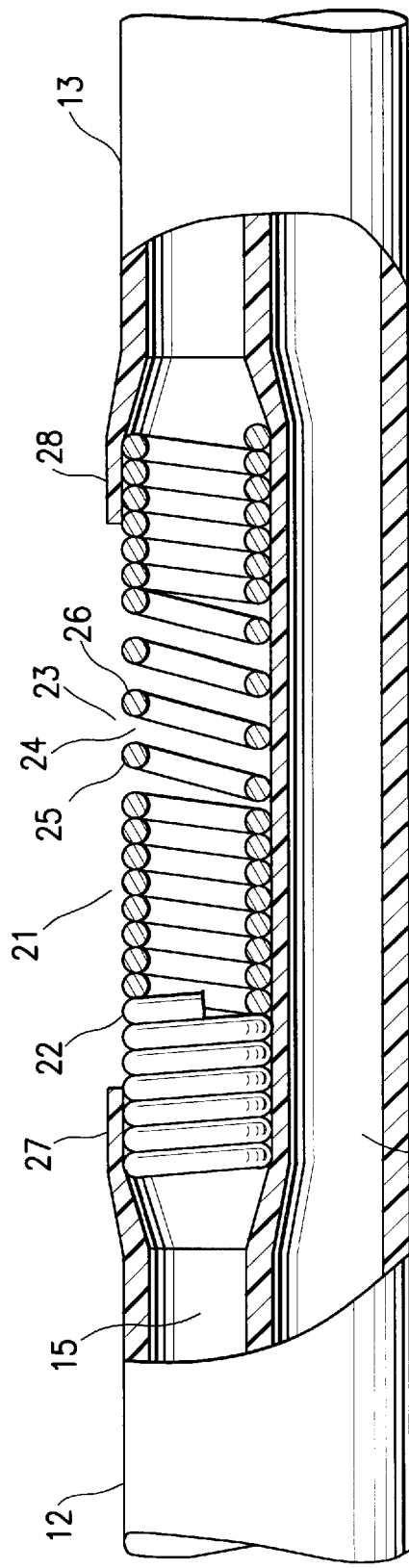
FIG. 5 is an enlarged longitudinal cross-sectional of the embodiment shown in FIG. 1 within the ellipse 5—5.

Reference is made to FIGS. 1–5 which depict a dilatation catheter 10 embodying features of the invention. In particular, the catheter 10 includes an elongated catheter shaft 11 with a relatively long proximal shaft section 12, a relatively short distal shaft section 13 and an intermediate shaft section 14 disposed between the proximal and distal shaft sections. The catheter shaft 11 has a first guidewire receiving inner lumen 15 which extends from the proximal end to the distal end of the catheter shaft and a second, inflation lumen 16 extending from the proximal end of the catheter shaft to a location spaced proximally from the distal end. A guidewire port 20 is provided in the distal end of the catheter shaft 11 which is in fluid communication with the first guidewire receiving lumen 15. The distal shaft section 13 is provided with a dilatation balloon 17 which has an interior 18 in fluid communication with the second inflation lumen 16 through opening 19. A guidewire 40 is slidably disposed within the first guidewire receiving inner lumen 15. The intermediate shaft section 14 has a longitudinally extendable portion 21 defined by helical coil 22 which has an expanded coil portion 23 forming a second guidewire port 24 between adjacent turns 25 and 26.. As shown in more detail in FIG. 5, the distal end 27 of the proximal shaft section 12 and the proximal end 28 of the distal shaft section 13 extend over the proximal and distal ends respectively of the helical coil 22 to hold the coil in place. Preferably, the distal end 27 and the proximal end 28 are bonded to the ends of the coil 22 by a suitable adhesive (not shown). However, other means may be employed, for example, the distal and proximal ends 27 and 28 may be heat shrunk onto the distal ends of the coil. A wide variety of other means may be employed to secure the coil 22 within the intermediate shaft section to prevent its displacement.

Figure 6:
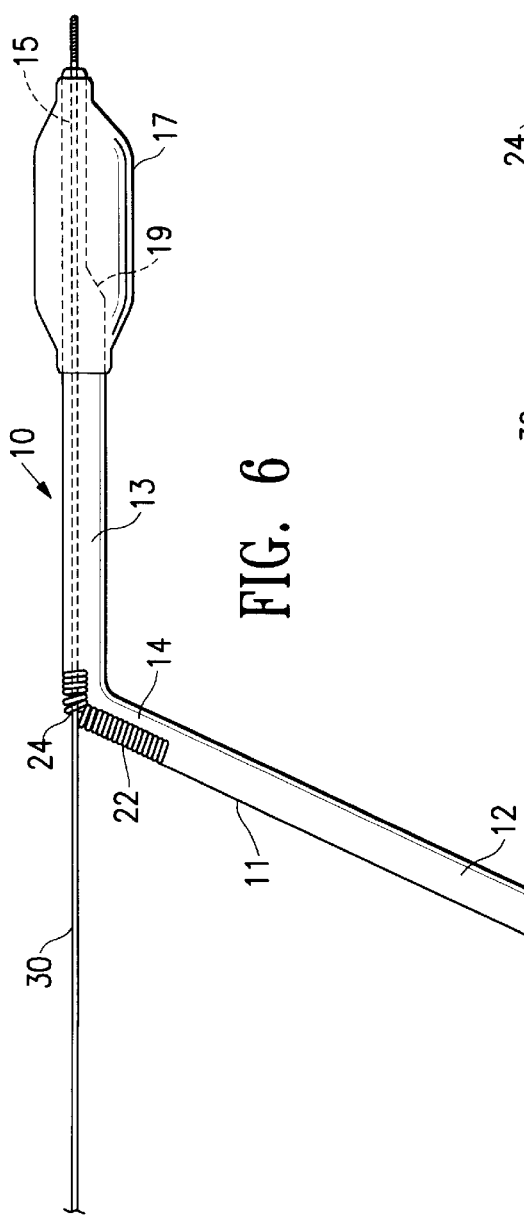
FIG. 6 is an elevational view of the embodiment shown in FIG. 1 with the distal shaft section being articulated with respect to the proximal shaft section and the proximal extremity of a guidewire extending out an opening in an intermediate shaft section.

FIG. 6 illustrates the dilatation catheter 10 shown in FIGS. 1–5 with the distal shaft section 13 articulated with respect to the proximal shaft section 12 with a guidewire 30 slidably disposed within the portion of the first or guidewire receiving inner lumen 15 extending in the distal shaft section and part of the intermediate shaft section 14. The intermediate shaft section 14 is bent at an angle of about 30 to about 150 degrees to ensure that the proximal end of the guidewire 30 is readily guided out of the proximal guidewire opening or port 24. The helical coil 22 preferably has sufficient resiliency to spring back into a relatively straight position when the force applied to the catheter 10 to cause the articulation of the proximal and distal shaft sections is released.

Figure 7:
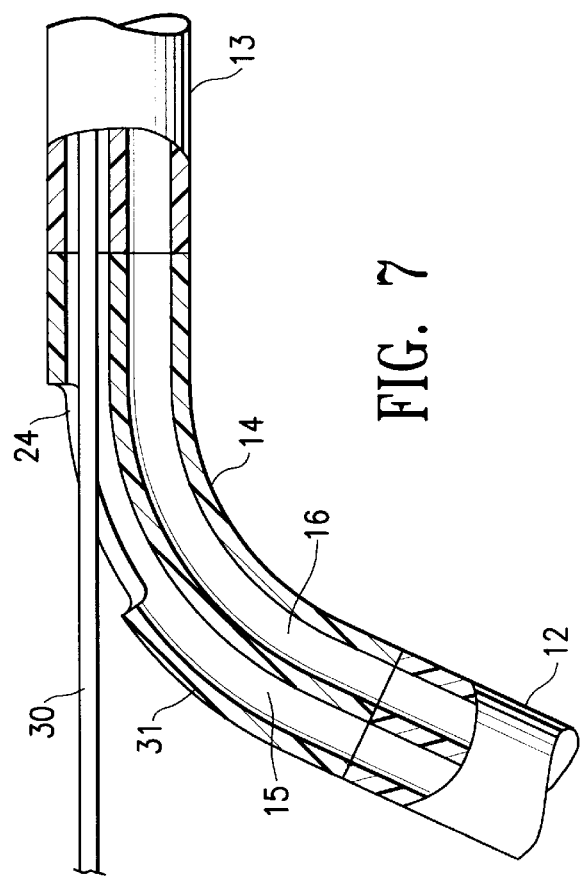
FIG. 7 is an elevational view, similar to that shown in FIG. 6, of an alternative embodiment wherein an intermediate shaft section having a proximal guidewire opening has an elastically and longitudinally expandable wall portion to facilitate the articulation of the proximal and distal shaft sections without kinking.

An alternative embodiment of the invention is shown in FIG. 7 wherein the first or guidewire lumen 15 is defined in part by an elastic wall portion 31 which has the second guidewire opening 24.

The use of the catheters of the invention for the most part follow the procedures described in U.S. Pat. No. 5,135,535 (Kramer), assigned to the present assignee (Advanced Cardiovascular Systems, Inc.), which has been incorporated by reference.

The catheter shaft can be formed by conventional techniques, e.g. extruding, from a variety of polymer materials already found useful in intravascular catheters such as polyethylene, polyimide, polyamide, PVC, polyesters (e.g. Hytrel) and high strength polymers such as polyetheretherketone (PEEK). The various components of the catheter can be joined by conventional adhesives, such as acrylonitrile based adhesives, heat shrinking, fusion bonding and the like.

The transverse dimensions of the catheter shaft 11 and the guidewire receiving inner lumen 14 are for the most part determined by the transverse dimensions of the guidewire to be used with the catheter. Typically, the guidewire is about 0.008 to about 0.035 inch (0.2–0.9 mm) in diameter. The guidewire lumen is configured to slidably receive the guidewire, i.e. it should be about 0.001 to about 0.005 inch (0.025–0.013 mm) larger than the guidewire diameter. The catheter shaft is sufficiently long to extend from outside the proximal end of a guiding catheter, which likewise extends out of the patient during the procedure, to a vascular location where the procedure is to be performed. Typically, the catheter is about 135 cm in length.

While the invention is described herein in terms of a dilatation catheter, those skilled in the art will recognize that it is application to a variety of intravascular catheters. Additionally, various modifications and improvements can be made to the present invention without departing from the scope thereof. Although individual features of embodiments of the invention may be shown in some of the drawings and not in others, those skilled in the art will recognize that individual features of one embodiment of the invention can be combined with any or all the features of another embodiment.

What is claimed is:

1. An intravascular catheter comprising:
   a) An elongated shaft having proximal and distal ends, a first port in the distal end, a first lumen extending therein to the first port in the distal end and a second lumen extending therein to a location proximally spaced from the distal end, the shaft comprising:
      i) an elongated proximal shaft section;
      ii) a relatively short distal shaft section having means to perform an intravascular procedure in communication with a portion of the second lumen extending therein; and
      iii) an intermediate, bendable, relatively longitudinally incompressible shaft section having a longitudinally extendable wall portion defining at least in part the first lumen with a second port therein and being sufficiently radially rigid to minimize kinking thereof upon bending of the intermediate shaft section and articulation of the distal shaft section with respect to the proximal shaft section which longitudinally expands the wall portion.

2. The intravascular catheter of claim 1 wherein the second port in the wall of the intermediate shaft section is spaced proximally at least about 10 cm from the distal end of the catheter shaft.

3. The intravascular catheter of claim 1 wherein the longitudinally extendable wall of the intermediate shaft section is formed at least in part of a helical coil.

4. The intravascular catheter of claim 3 wherein the second port in the longitudinally extendable wall of the intermediate shaft section is formed by expanded adjacent turns of the helical coil.

5. The intravascular catheter of claim 1 wherein means to perform an intravascular procedure are provided on the distal shaft section.

6. A balloon dilatation catheter which can be used in an over-the-wire or rapid exchange mode comprising:
   a) an elongated shaft having proximal and distal ends, a guidewire port in the distal end, a guidewire receiving lumen extending therein to the guidewire port in the distal end and an inflation lumen extending therein to a location spaced proximally from the distal end, the shaft comprising
      i) a proximal shaft section;
      ii) a relatively short distal shaft section with a dilatation balloon having an interior in fluid communication with a portion of the inflation lumen extending therein; and
      iii) an intermediate, bendable, relatively longitudinally incompressible shaft section between the proximal shaft section and the distal shaft section having a longitudinally extendable wall portion defining at least in part a portion of the guidewire receiving lumen extending therein and a second port therein and which is sufficiently radially rigid to minimize kinking thereof upon bending of the intermediate shaft section and articulation of the distal shaft section with respect to the proximal shaft section.

* * * * *